(12) United States Patent
Vilambi et al.

(10) Patent No.: US 6,394,994 B1
(45) Date of Patent: May 28, 2002

(54) METHOD FOR TESTING THE ABILITY OF AN IONTOPHORETIC RESERVOIR-ELECTRODE TO DELIVER A MEDICAMENT

(75) Inventors: Nrk Vilambi, Jamaica Estates, NY (US); Bruce M. Eliash, Franklin Lakes; Preston Keusch, Hazlet, both of NJ (US); Lue Huai Li, Brooklyn, NY (US); Elena N. Chabala, Jersey City; Uday K. Jain, Mahwah, both of NJ (US); Louis J. Mestichelli, Doylestown, PA (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

(21) Appl. No.: 09/384,765

(22) Filed: Aug. 27, 1999

(51) Int. Cl.[7] .............................................. A61M 31/00

(52) U.S. Cl. ...................... 604/501; 604/20; 604/891.1; 128/898

(58) Field of Search .......................... 604/20, 500, 501, 604/890.1, 891.1, 892.1; 128/898

(56) References Cited

U.S. PATENT DOCUMENTS

| | | | | |
|---|---|---|---|---|
| 5,169,383 A | * | 12/1992 | Gyory et al. ................. | 604/20 |
| 5,693,024 A | | 12/1997 | Flower ........................ | 604/20 |

OTHER PUBLICATIONS

Standardized Quality Control Drug Release Testing from Commerical Iontophoretic Drug Delivery Systems, L.B. Lloyd, D.J. Miller and T.M. Parkinson, Dermion, Inc., 1290 West 2320 South, Salt Lake City, UT 84119.

* cited by examiner

Primary Examiner—Glenn K. Dawson
Assistant Examiner—Jennifer Maynard
(74) Attorney, Agent, or Firm—Kirkpatrick & Lockhart LLP

(57) ABSTRACT

A method for testing the ability of an iontophoretic reservoir-electrode to deliver a medicament includes providing an iontophoretic reservoir-electrode with a contact surface having a shape, a suitable electrical connection and a hydrated bibulous reservoir containing an ionized medicament. The method further includes providing another electrode operating a at preselected polarity opposite to the preselected polarity of the medicament reservoir-electrode. The method further includes providing a separation medium having the property of allowing passage therein to of ions of one charge. The separation medium is positioned between the reservoir electrode with the ionized medicament and the another electrode. The method also includes applying a sufficient electrical potential between the iontophoretic reservoir-electrode containing the ionized medicament and the another iontophoretic reservoir-electrode so that a current flows through the separation medium for a preselected time thereby transporting a quantity of the ionized medicament into the separation medium. The method then includes determining an amount of the ionizable medicament in the separation medium.

24 Claims, 8 Drawing Sheets

METHOD FOR TESTING THE ABILITY OF AN IONTOPHORETIC RESERVOIR-ELECTRODE TO DELIVER A MEDICAMENT

FIELD OF INVENTION

The present invention is generally related to drug delivery and more specifically to iontophoretic delivery of a medicament.

BACKGROUND

Iontophoretic delivery of a medicament is accomplished by application of a voltage to a medicament loaded reservoir-electrode, sufficient to maintain a current between the medicament loaded reservoir-electrode and a return electrode (another electrode) applied to a patient's skin so that an ionic form of the desired medicament is delivered to the patient.

An iontophoretic device loaded with a medicament, from a pharmaceutical point of view, may be considered as analogous to a tablet, a passive transdermal patch or a pre-filled syringe, i.e., a unit dose of the particular medicament for delivery into a single patient. Like the tablet, the transdermal patch or the pre-filled syringe, iontophoretic devices are a product of a multi-step manufacturing process. Accordingly, a concern of the manufacturer and the practitioner administering the dose of the medicament to the patient is: "Does the device, (tablet, passive transdermal patch or syringe) actually contain and is it capable of delivering the correct amount of the medicament?"

In the case of tablets, there are weight variation, content uniformity, dissolution tests and drug release tests. These tests have evolved into well-accepted methods and are published in the United States Pharmacopoeia. For a tablet, if the tablet weight is substantially uniform, the formulation that is used to prepare the tablet is correct and well mixed and the tablet disintegrates and releases the medicament, there can be a fair assurance that any individual tablet administered to a patient provides the desired dosage. For tablets, drug release tests are based on measuring the release of the medicament by diffusion into a medium under controlled conditions. For passive transdermal patches, which have the same drug release mechanism as oral dosage forms, the above standard tests have been modified and adapted to measure drug release.

An iontophoretic device presents a considerably more complex problem for analysis of drug release. While the test procedures described above and manufacturing controls can provide assurances that the formulation for the iontophoretic device is correct, well mixed and accurately applied to the device, the literature methods for measuring medicament release in tablets and passive transdermal devices are not suitable for study of iontophoretic drug delivery that depends upon ion migration in the presence of an electric field for drug transport. Ultimately it is necessary to determine if the iontophoretic device is capable of actually delivering the desired dose of the medicament under conditions indicative of the device's performance in actual use.

A published report by Lloyd, et al. from Transdermal Administration, A Case Study, Iontophoresis, March 1997 discloses an in vitro drug release test for commercial transdermal iontophoretic electrodes that the authors state is analogous to drug release tests used to evaluate passive drug release from commercial transdermal systems. In this paper, the authors relate the use of a glass double-sided diffusion cell containing a receptor solution that receives a delivery of lidocaine from an iontophoretic device. The authors relate that a difficulty they overcome in their method is discrimination between passive (diffusive) delivery of the medicament and the electrically driven iontophoretic delivery. The drug containing electrode is applied to polyvinylpyrollidone (PVP) coated polycarbonate microporous membrane on one side of the diffusion cell, with a return electrode applied to the other side of the diffusion cell. A current is generated through the cell and the concentration of the drug in the receptor solution is determined by an appropriate analytical method. The purpose of the PVP coated microporous membrane is to reduce the diffusional transport of the lidocaine from the reservoir-electrode into the receptor solution. The authors relate that their method provides ratios between 1.5:1 and 5:1 active iontophoretic delivery to passive diffusive delivery for the lidocaine present in their device in their test system into a diffusion cell containing aqueous sodium chloride as a receptor solution. The authors reported that the PVP coated porous membrane they used was the only membrane that was satisfactory, the other membranes, such as ion exchange membranes, either were unable to discriminate between active and passive delivery or were too resistive to allow an electric current to pass. The test as described in the paper required up to 120 minutes for each sample and the authors themselves state that there are many unresolved questions to be answered before a statistically valid test suitable for routine use is available.

The art of iontophoresis devices would be advanced if a rapid and reliably repeatable test were available. Such a method is disclosed hereinbelow.

SUMMARY

A method for testing the ability of an iontophoretic reservoir-electrode to deliver a medicament includes providing an iontophoretic reservoir-electrode. The reservoir-electrode includes a suitable electrical connection and a reservoir containing at least one ionized medicament. The method includes providing another suitable electrode. The method further includes providing a separation medium having the property of allowing a transport thereinto of the at least one ionized medicament under the influence of an applied electric current flowing therethrough compared to a transport of the ionized medicament thereinto in the absence of the applied electric current in a ratio greater than one. The method then includes placing the contact surface of the reservoir-electrode containing the ionized medicament in electrical contact with the separation medium and placing the separation medium in electrical contact with the another electrode. The method then includes applying a sufficient electrical potential between the iontophoretic reservoir-electrode containing the at least one ionized medicament and the another electrode so that a preselected current flows through the separation medium for a preselected time thereby transporting at least a portion of the at least one ionized medicament into the separation medium and determining an amount of the at least one ionized medicament in the separation medium.

The method of the invention provides differentiation between electrically driven (iontophoretic) and passive (diffusive) transport of the medicament, making it well suited as a test method for iontophoretic devices. The method of the invention is rapid and simple to practice. The method of the invention utilizes readily available and stable separation media as a sampling device in a simulated use condition. The ionized medicament is delivered to the separation medium by a preselected current and the amount determined. The method is compatible with a variety of assay methods. In one embodiment, the method allows a practitioner to apply a sufficient potential across the separation medium to cause a higher current than would be acceptable to deliver a particular medicament to a patient to transport the medicament into the separation medium. This higher rate of transport, available in the method of the invention, of the ionized medicament into the separation medium facilitates assay of multiple samples of reservoir-electrodes by minimizing the time required to prepare a series of individual samples for analysis. The ability to use the higher rate of transport has the additional benefit of facilitating the differentiation between the active (electrically driven) transport and the passive (diffusive) transport of the medicaments. Further, the method is applicable to iontophoretic devices having various shapes, sizes, and configurations of the active medicament charged reservoir-electrode and the return electrode without complicated and possibly confounding modifications to the device being tested. Additionally, the use of the separation medium as a sampling device in the method of the invention is readily amenable to widely used automated extraction, sampling and assay equipment.

DETAILED DESCRIPTION

Figure 1:
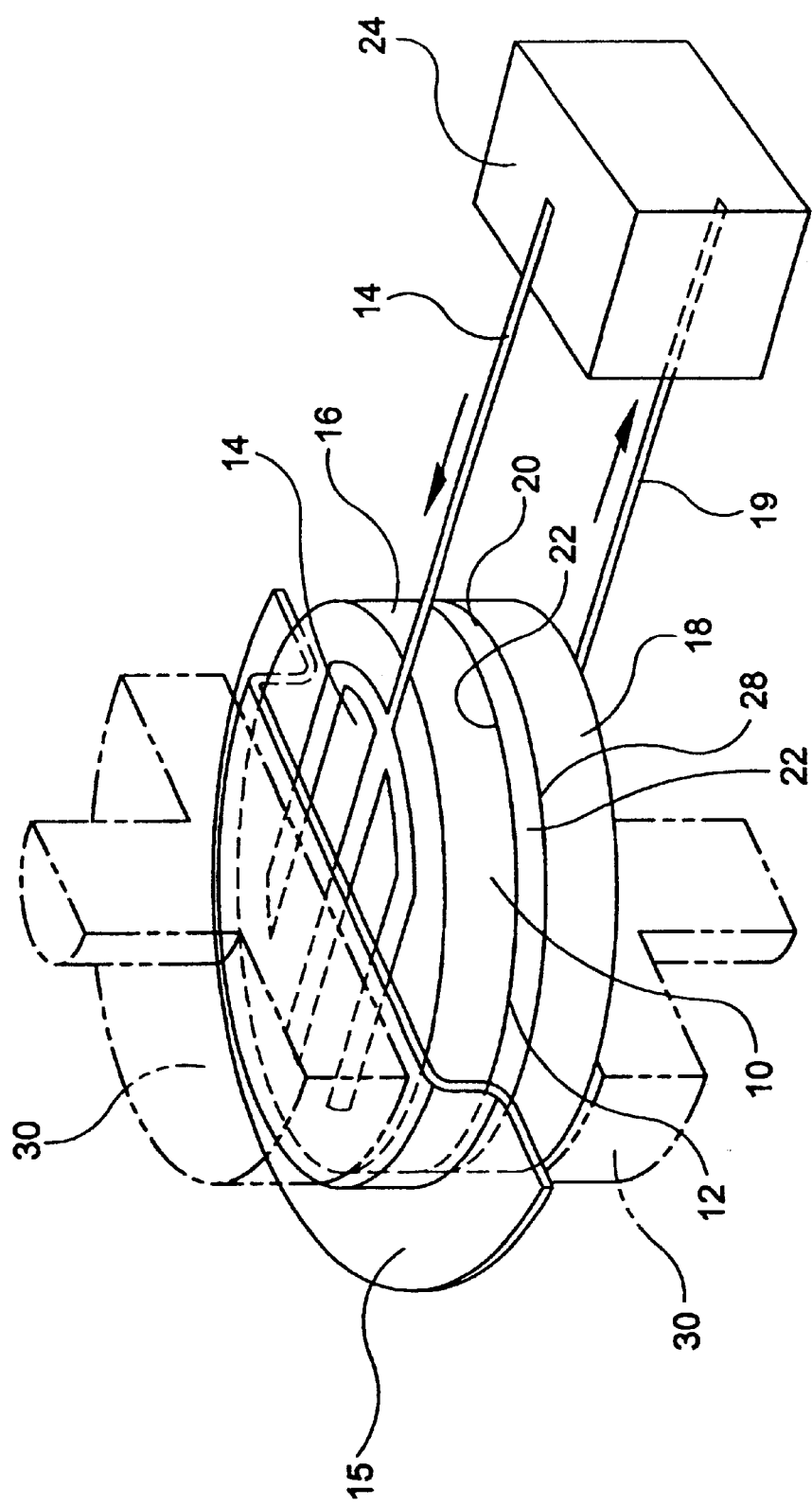
FIG. 1 is a schematic perspective view of an active reservoir-electrode, a separation medium and another electrode mounted in a fixture as a system for iontophoretic transport.

While this invention is satisfied by embodiments in many different forms, there is shown in the drawings and is herein described in detail, a preferred embodiment of the invention with the understanding that the present disclosure is to be considered exemplary of the principles of the invention and is not considered to limit the invention to the embodiment illustrated. The scope of the invention is measured by the appended claims and their equivalents.

Referring to FIGS. 1–4, a method of the present invention for testing the ability of an iontophoretic reservoir-electrode 10 to deliver a medicament includes providing iontophoretic reservoir-electrode 10 having a contact surface 12. Reservoir-electrode 10 includes a suitable electrical connection 14 and a reservoir 16 containing at least one ionized medicament with either a net positive charge or a net negative charge at a preselected pH range. In the preferred embodiment illustrated in FIGS. 1 and 2, suitable electrical connection 14 is a formed film including silver and silver chloride that is applied to a backing 15 used to attach iontophoretic reservoir-electrode to a patient and contain reservoir 16. Reservoir 16 may be a hydrogel, a rigid or flexible porous charged with a medicament solution, or any other material suitable for containing and releasing the medicament. Preferably, reservoir 16 is a hydrogel. A suitable hydrogel for forming reservoir 16 is formed from cross-linked polyvinylpyrrolidone. The method includes providing another suitable electrode 18 also preferably having a contact surface 20. Another electrode 18 also may be formed from a hydrogel similar to that used for reservoir 16, or other materials either formed from or in electrical contact with materials suitable for ion conduction including contained solutions.

Figure 2:
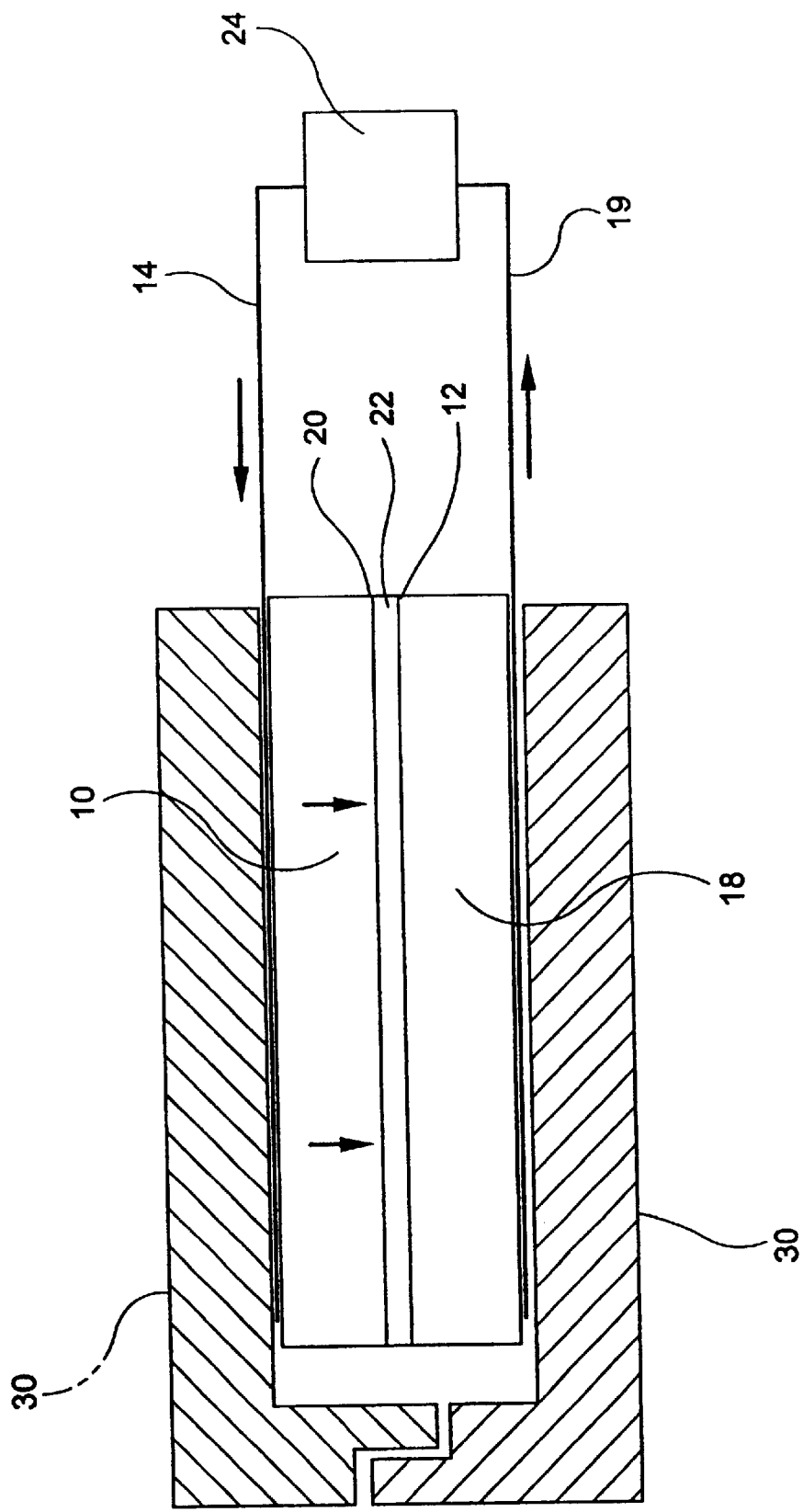
FIG. 2 is a schematic view of the of the reservoir-electrode system from FIG. 1 illustrating the current flow.

The method further includes providing a separation medium 22 having the property of allowing a transport thereinto of the at least one ionized medicament under the influence of an applied electric current, indicated by the arrows in FIGS. 1 and 2, flowing therethrough compared to a transport of the ionized medicament in the absence of the applied electric current in a ratio greater than one. The method then includes placing contact surface 12 of reservoir-electrode 10 in contact with separation medium 22 and placing separation medium 22 in electrical and, preferably physical contact, with contact surface 20 of another electrode 18. In the preferred embodiment of this method, another electrode 18 is similar in construction to reservoir-electrode 10 and is charged with a suitable salt instead of a medicament. Another electrode 18 includes a suitable electrical connection 19. In the preferred embodiment illustrated in FIG. 1, suitable electrical connection 19 for another electrode 18 is preferably a formed silver/silver chloride printed ink electrode similar to electrical connection 14 in reservoir-electrode 10. As is the case with connection 14, electrical connection 19 may also be formed from metallic materials including copper, platinum, aluminum, silver and the like and in the form of wire, foils, mesh, non-metallic conductors such as carbon, metal/metal halide combinations or conductive inks including metallic materials, non-metallic conductors, salts and other conductive particles as well as combinations of these materials.

The method then includes applying a sufficient electrical potential with a power source 24 between iontophoretic reservoir-electrode 10 containing the at least one ionized medicament and another electrode 18 so that a preselected current, indicated by arrows in FIGS. 1 and 2, flows through separation medium 22 for a preselected time thereby transporting at least a portion of the at least one ionized medicament into separation medium 22 and determining an amount of the at least one ionized medicament in the separation medium.

Figure 3:
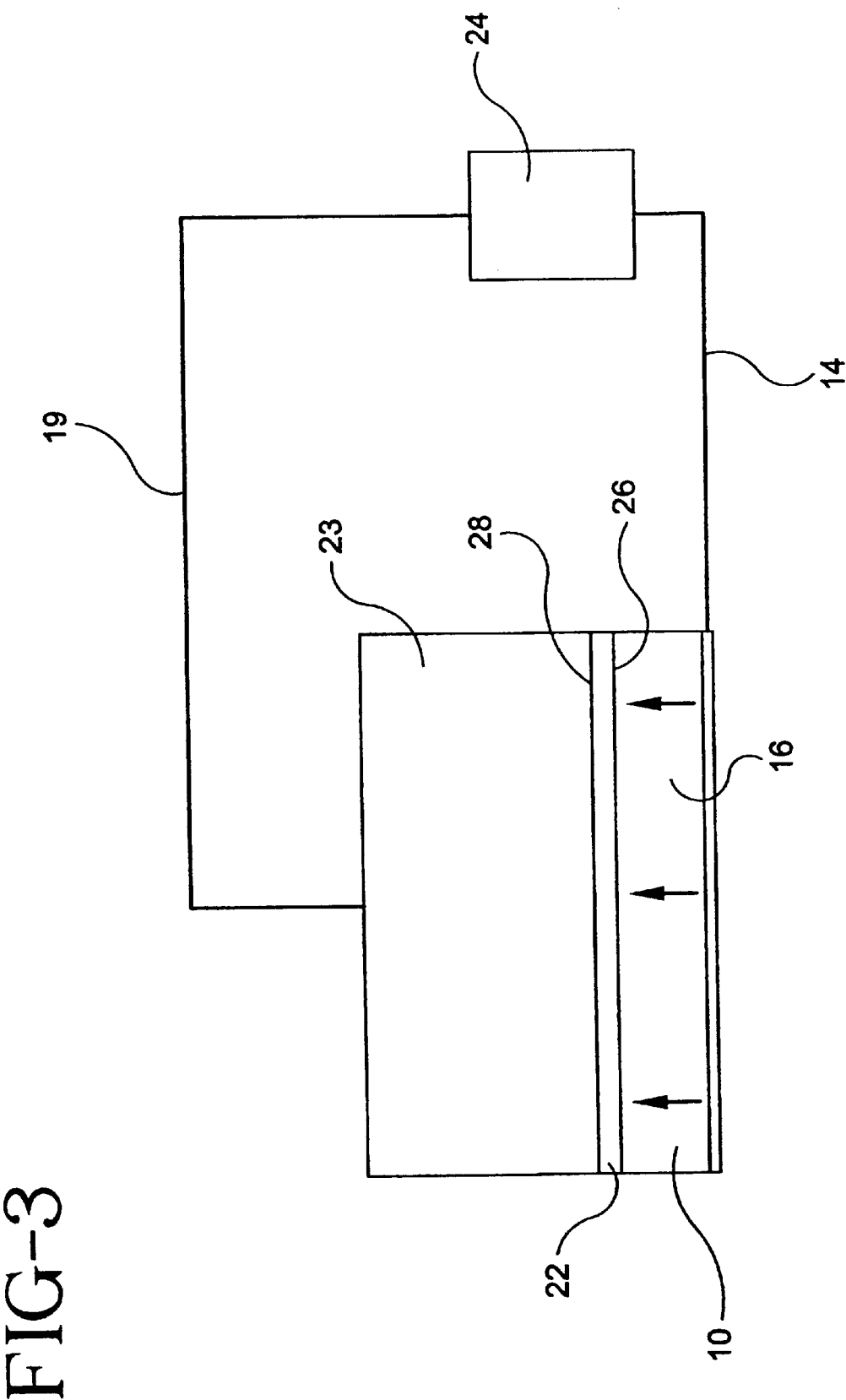
FIG. 3 is a schematic view of another arrangement of an active reservoir-electrode, a separation medium and another electrode useful for practicing the method of the invention.
Figure 4:
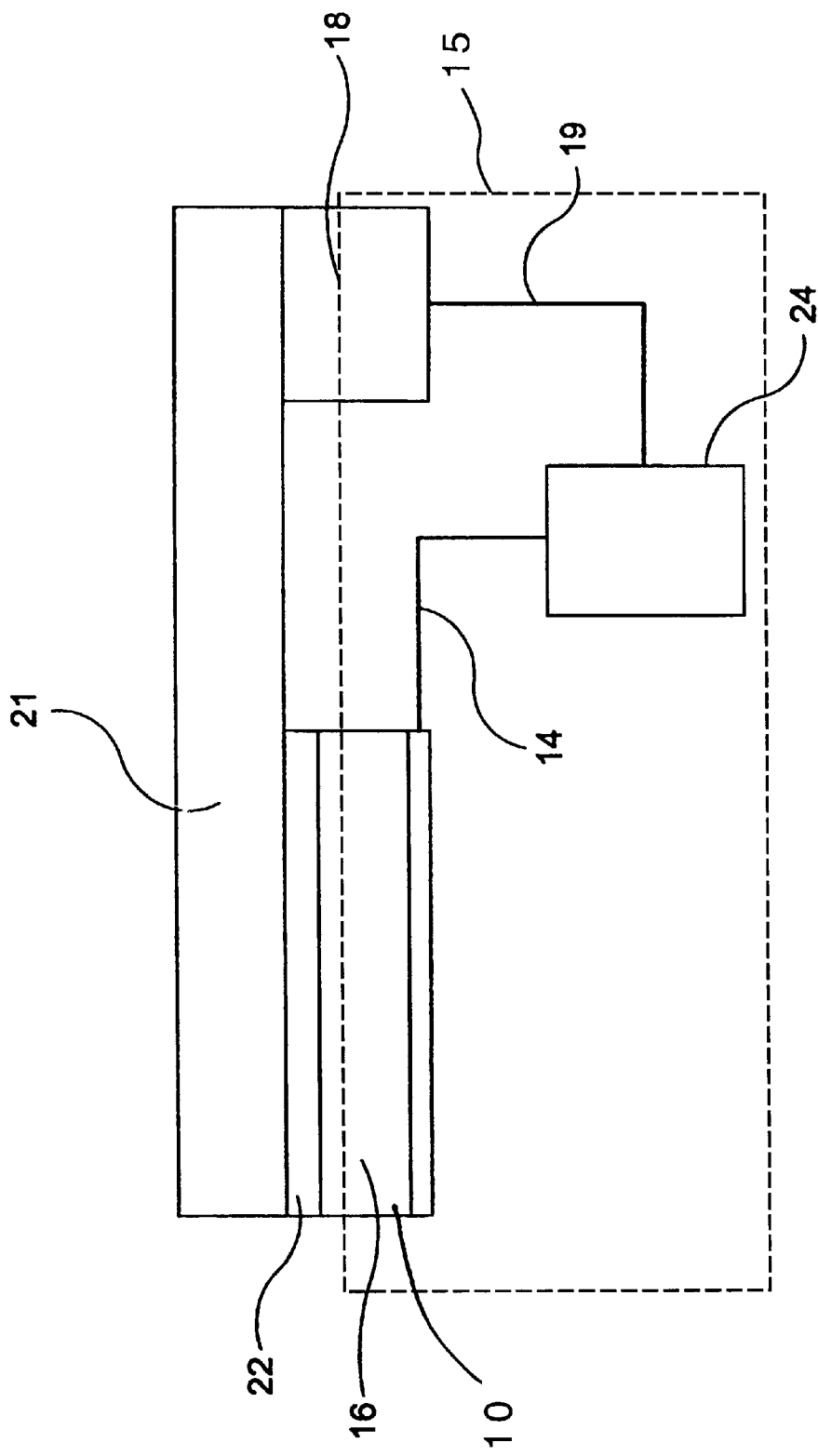
FIG. 4 is a schematic view of a further arrangement of an active reservoir-electrode, a separation medium and another electrode also useful for practicing the method of the invention.

Referring now to FIGS. 3 and 4, alternative placements of reservoir-electrode 10, separation medium 22 and another electrode 18 are shown. While direct physical and electrical contact between the separation medium and electrode 18 is preferred in the example disclosed below and illustrated in FIGS. 1 and 2, since the current flowing in the reservoir-electrode, separation medium and the return electrode is carried by the flow of ions, an electrical connection between two or more of the reservoir-electrode, separation medium and the return electrode may be completed by a section 21 of a conductive material capable of ion current transmission such as a hydrogel, a contained solution 23 or the like. In the case where the method of the invention is used on a self-contained flexible iontophoretic device that includes both an active and a return electrode, the transport of the charged medicament into the separation medium may be facilitated by the use of section 21 of a hydrogel material to form the electrical connection between one or more of the reservoir-electrode, the separation medium or return electrode. FIGS. 3 and 4, show alternate placements of reservoir-electrode 10, separation medium 22 and another electrode 18, that may be preferred for particular reservoir-electrodes and medicaments where the contact between separation medium 22 and another electrode 18 is electrical. In FIG. 3, a placement of reservoir-electrode 10 with separation medium 22 and a contained ionic solution 23 disposed on second side 28 of separation medium 22 a schematic cross-sectional illustrates reservoir-electrode. FIG. 4 schematically illustrates a complete iontophoretic device 40 with a controlled power supply 24 that includes both active reservoir-electrode 10 and return electrode 18 disposed on backing, indicated in phantom, 15. The placement of section 21 of a conductive hydrogel to form the electrical connection between separation medium 22 disposed on contact surface 12 of reservoir-electrode 10 and another electrode 18 simplifies the analytical evaluation of complete device 40 without any physical disruption to the device that may introduce confounding errors into the analytical measurement.

Separation medium 22 preferably is an ion exchange membrane such as a radiation-grafted cast film formed from polytetrafluoroethylene (PTFE). A suitable radiation grafted PTFE film is available from Pall Specialty Materials, East Hills, N.Y. as "IonClad" R-4010. The radiation-grafted cast PTFE film has ionic functional groups grafted throughout the PTFE. Other suitable ion exchange membranes include, but are not limited to, "Neosepta", available from Tokuyama Soda Co. LTD., Tokyo, Japan; "Membrane ESC 7000/ESC 7001" available from Electrosynthesis, East Amherst, N.Y.; and "Nafion", available from E.I. duPont, Wilmington, Del. Other suitable separation media include, but are not limited-to ion exchange resins, ion exchange beads, polyelectrolyte salts with ion exchange capability, hydrogels, semipermeable membranes and the like.

Preferably, reservoir-electrode 10 contact surface 12 and another electrode 18 contact surface 20 are placed in physical and electrical contact with one of a first side 26 and a second side 28 of separation medium 22 which preferably is an ion exchange membrane. A fixture 30, best seen in FIGS. 1 and 2, preferably is provided to locate the electrode contact surfaces against separation medium 22 and to apply sufficient pressure to reservoir-electrode 10 and another electrode 18 to ensure sufficient intimate physical and electrical contact between reservoir-electrode 10, separation medium 22 and another electrode 18 to optimize the transport of the ionized medicament and current flow.

Figure 5:
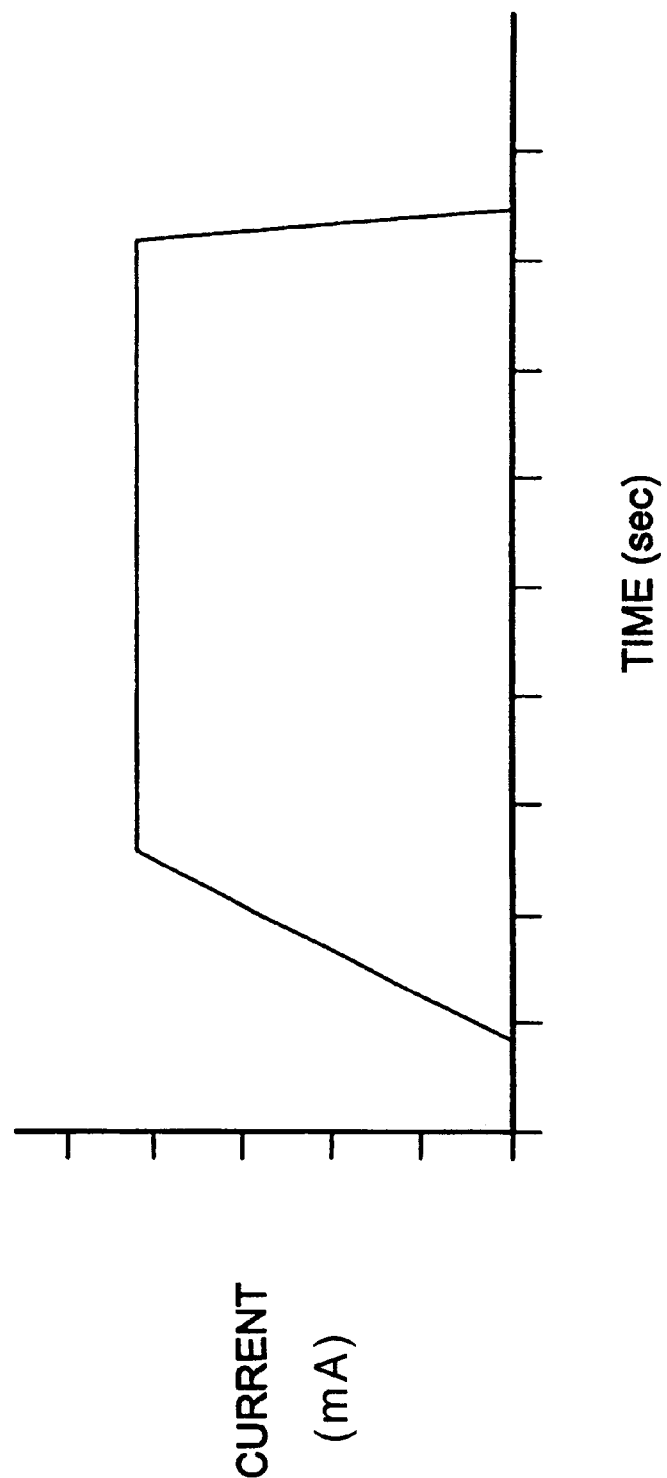
FIG. 5 is a graphical representation of a preselected current flow profile during an iontophoretic delivery as illustrated in FIG. 1.
Figure 6:
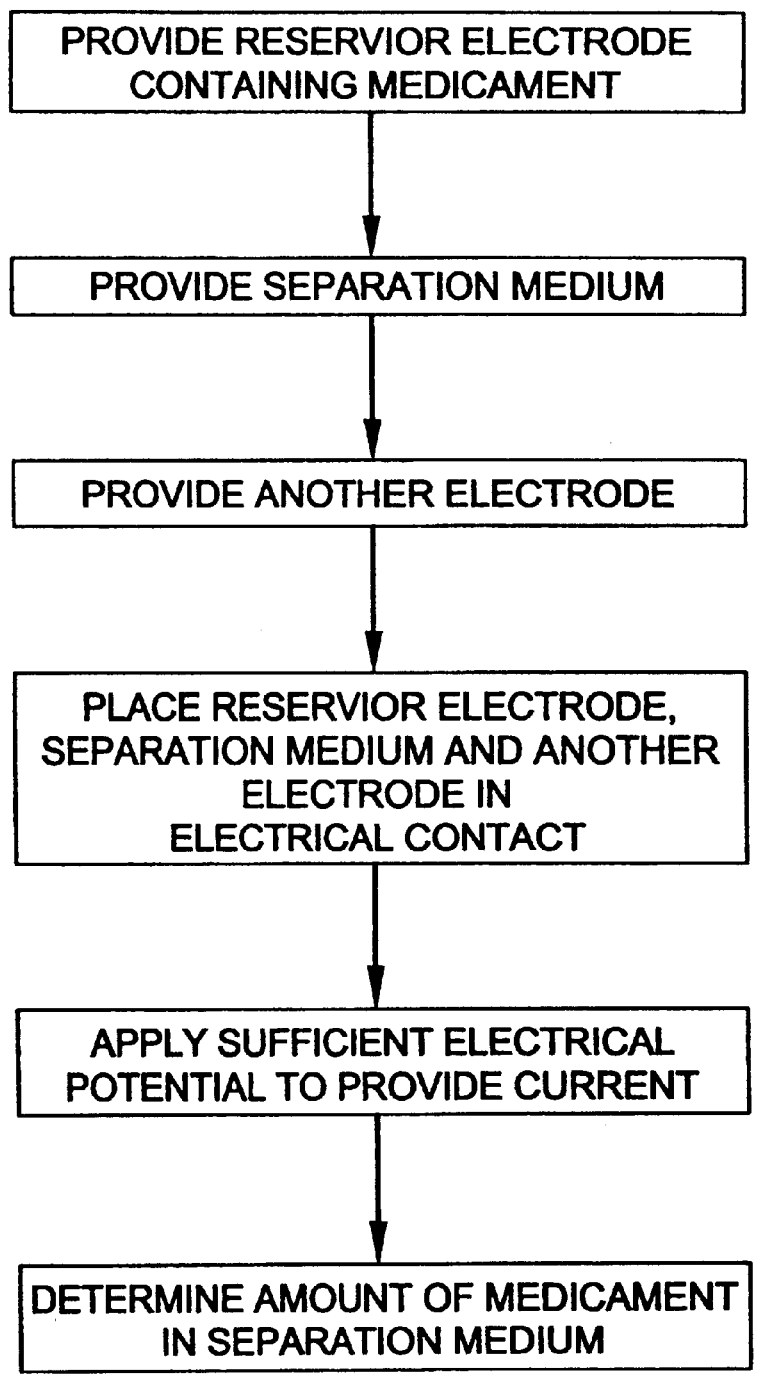
FIG. 6 is a flow chart descriptive of the method of the invention.

The applying of a sufficient electrical potential at connection 14 across reservoir-electrode 10, separation medium 22 and another electrode 18 at connection 19 to cause a preselected current to flow between the electrodes through separation medium 22 for the method of the invention may be accomplished in several ways. A power source 24 used in the method of the invention may be a laboratory constant current generator, a battery, an iontophoretic power supply, or a programmable laboratory power source. Referring to FIG. 5, a graphical representation of a typical preselected current is shown. In this example, sufficient voltage is applied to initiate a current to a preselected value in the circuit. The power supply then maintains a constant current in the circuit for a preselected period of time, after which the voltage is decreased and the current decreases and ceases. In practicing the method of the invention, preferably, a practitioner applies sufficient voltage to cause a preselected current flow that may be higher than a current suitable for use in iontophoretic delivery of the medicament to a patient. For the method of the invention, the benefit of the preselected higher current flow is that the transport of the at least one medicament from reservoir-electrode 10 into separation medium 22 can be accomplished in a shorter time.

As was discussed above, the active transport, i.e., the transport of the medicament due to the action of the electric current, of the at least one medicament from reservoir-electrode 10 into separation medium 22 is greater than the passive or diffusive transport of the at least one medicament from reservoir-electrode 10 into separation medium 22. Since the purpose of the test method of the invention is to determine the amount of the ionized medicament transported by the action of the current flow, the higher current flow with the resultant shorter time for delivery minimizes the effect of the passive or diffusive transport on any amount of the at least one ionized medicament that maybe transported into separation medium 22 by passive or diffusive transport.

A series of assays on reservoir-electrodes containing lidocaine HCl and epinephrine bitartrate using an example of the method of the invention is given below. The presentation of this specific method is not intended to be limitative of the method to the particular medicaments, salts of the medicaments, conditions, separation media and reagents used, rather it is exemplary of the use of a separation medium to acquire an assay sample in the method of the invention.

1) A series of iontophoretic reservoir-electrodes formed from a hydrated cross-linked polyvinylpyrrollidone (PVP) laminated onto silver/silver chloride electrodes were prepared. Each of the reservoir-electrodes had a contact surface area of about five square centimeters and each was loaded with about 100 mg of lidocaine HCl and about 1.05 mg of epinephrine, as epinephrine bitartrate, and suitable inactive excipients. Each of the reservoir-electrodes had a suitable electrical connection. These reservoir-electrodes were submitted for evaluation as active reservoir-electrodes.

2) A series of iontophoretic reservoir-electrodes, physically identical to the active reservoir-electrodes, were prepared and charged with 0.18% (w/w) aqueous sodium chloride to function as return (another) electrodes for the medicament charged active electrodes.

3) A separation membrane was selected. Ion exchange membrane (R-4010, Pall Specialty Materials, and NY), a cation exchange membrane, was provided. A cation exchange membrane was selected since lidocaine and epinephrine ions have a net positive charge in the reservoir-electrode, thus selectively facilitating these ions passage into the membrane. In the case where the target medicaments have a net negative charge, an anion exchange membrane would be selected as a separation medium. The ion exchange membranes used in this example were received in the acid form and pretreated for active (iontophoretic) testing by exposure to normal (aqueous 0.9% w/w) saline for 24 hours at ambient conditions.

4) The pretreated ion exchange material was cut into sections having a five square centimeter area with a similar shape to the contact area of the active and return reservoir-electrodes to provide an individual ion exchange membrane for each variant of the experiment. The ion exchange membranes may be pretreated in bulk or as individual pieces. The primary constraint on the shape of the ion-exchange membrane is that the separation membrane be of sufficient size to prevent direct physical contact between the active reservoir-electrode containing the medicament and the return electrode so that all of the current passes through the separation medium.

5) An active reservoir-electrode was placed in a fixture along with a separation membrane and return reservoir-electrode so that the contact surfaces of the reservoir-electrodes were on opposite sides of and in intimate physical and electrical contact with the membrane for each of the preselected exposure times. The fixture applies a sufficient load to the reservoir-electrodes to ensure the desired contact between the reservoir-electrode contact surfaces and the ion exchange membrane.

6) A Hoefer Scientific Power supply PS500x was affixed to the electrical contacts of the reservoir-electrodes with the polarity preselected so that the reservoir-electrode containing the lidocaine HCl and the epinephrine bitartrate serves as the anode and the other electrode with the sodium chloride serves as the cathode to complete the circuit.

7) A series of experiments were conducted with the active (current present) delivery for several preselected time periods and compared to similar time periods with no current flow (passive or diffusive delivery).

8) After each of the several preselected exposure times of active (current present) and passive (no current) of the reservoir-electrode with the placement in the fixture, the ion exchange membranes were removed from the fixture and extracted in a suitable extraction solvent. In the present case, aqueous acetonitrile buffered with acetate buffer to a pH of about 3.4 was selected. For other ionized medicaments, other extraction solvents may be preferred.

9) Each ion exchange membrane was placed in was placed in 50 ml of the extraction solvent and gently stirred for a sufficient time to elute the lidocaine and the epinephrine into the aqueous buffered acetonitrile.

10) The aqueous buffered acetonitrile eluent was then assayed by High Pressure Liquid Chromatography (HPLC) for the lidocaine content and the epinephrine content. Other extraction and assay techniques for the assay may be envisioned and are considered to be within the scope of the method of the invention.

Results of these assays for lidocaine HCl given below in Table 1 at several times and conditions.

TABLE 1

| Current (mA) | Contact time (min) | Lidocaine HCl (n = 3, mg) Mean ± SD | Ratio (active/passive) |
|---|---|---|---|
| 0 (passive) | 1.5 | 0.39 ± 0.05 | |
| 12 (active) | 1.5 | 2.39 ± 0.08 | 6.2 |
| 0 (passive) | 1.0 | 0.32 ± 0.05 | |
| 18 (active) | 1.0 | 2.47 ± 0.09 | 7.7 |
| 0 (passive) | 0.67 | 0.25 ± 0.02 | |
| 27 (active) | 0.67 | 2.62 ± 0.09 | 10.3 |

Comparative assay results of three different lots of ion exchange membrane with reservoir-electrodes from a single lot containing lidocaine HCl and epinephrine bitartrate are given below in Table 2.

TABLE 2

| Lot # | Lidocaine HCl (mg) Mean ± SD, n = 3 | Epinephrine (mg) Mean ± SD, n = 3 |
|---|---|---|
| 1 | 2.46 ± 0.02 | 0.020 ± 0.001 |
| 2 | 2.38 ± 0.05 | 0.017 ± 0.001 |
| 3 | 2.37 ± 0.04 | 0.018 ± 0.001 |

The results from these examples show that the method of the invention is discriminatory between the active and passive transport of the medicament into the separation medium and is capable of sufficient precision to be useful for routine evaluation of production reservoir-electrodes. Further, the data shows that the method is useful for determination of more than one medicament present in the reservoir-electrode. Table 1 indicates that as the current is increased and the time is reduced, while maintaining the total charge delivered as a constant, the separation ratio (active/passive) increases. The increase in the separation ratio is likely due to the reduced passive diffusion that results from shorter contact times. In normal therapeutic use, the lidocaine/epinephrine charged reservoir-electrode of the example is used for a delivery time of ten minutes at about 1.8 milliamps (mA) current or 18 mA-minutes. The data presented in the example shows that for the purpose of the method of the invention, shorter delivery times with higher currents are able to provide meaningful and repeatable test results. Additionally, Table 2 illustrates that the method is not sensitive to lot-to-lot variation in the separation medium.

While the example given above illustrates the method of the invention for confirming the function of an iontophoretic reservoir-electrode by delivering two ionized medicaments, lidocaine HCl and epinephrine bitartrate, into a separation medium, then determining the amount of the ionized medicament in the separation medium, the method of the invention is applicable to other anesthetic agents, anti-inflammatory agents, anti-infectives, psychoactives, anti-diabetic, anti-cancer, anti-thrombotic, anti-obesity, growth hormone, or any other medicament or combination of medicaments that may be delivered with either an anodic (for medicaments having a net positive charge) or cathodic (for medicaments having a net negative charge) active electrode. Examples of these types of medicaments include for example, suitable salts of fentanyl, dexamethasone, insulin, heparin, luteinizing hormone-releasing hormone, parathyroid hormone, calcitonin, bisphonphonates and the like.

Figure 7:
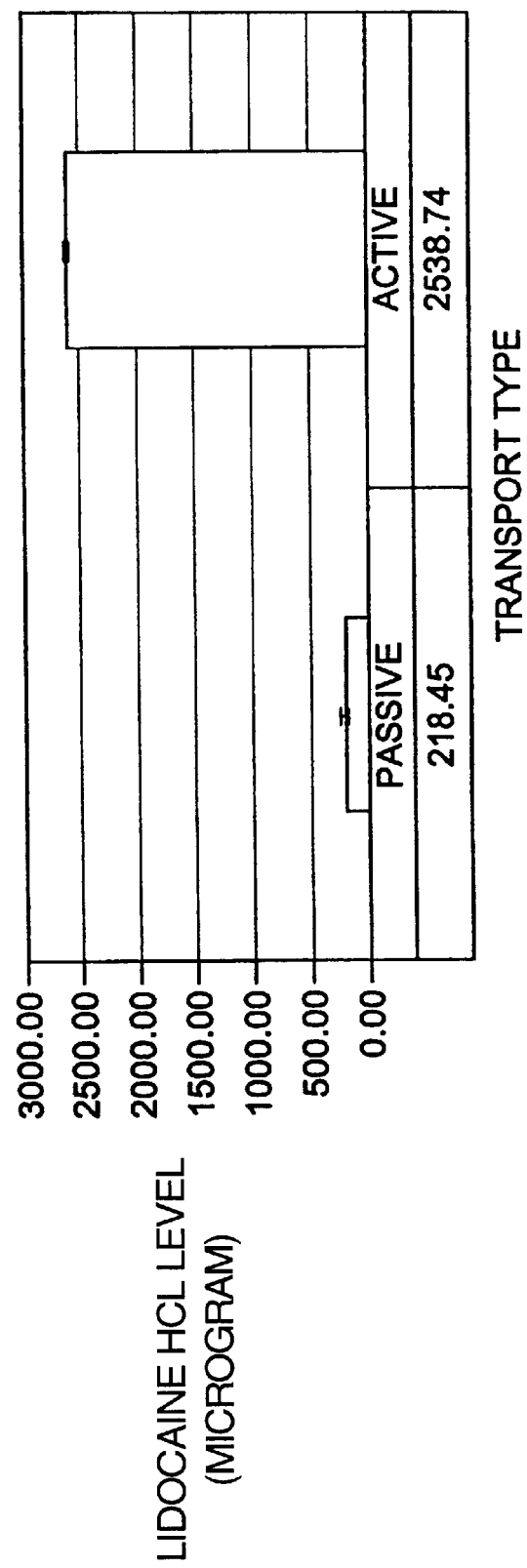
FIG. 7 is a graphical representation of the relative amounts of active versus passive delivery of Lidocaine HCl seen in one embodiment of the method of the invention.
Figure 8:
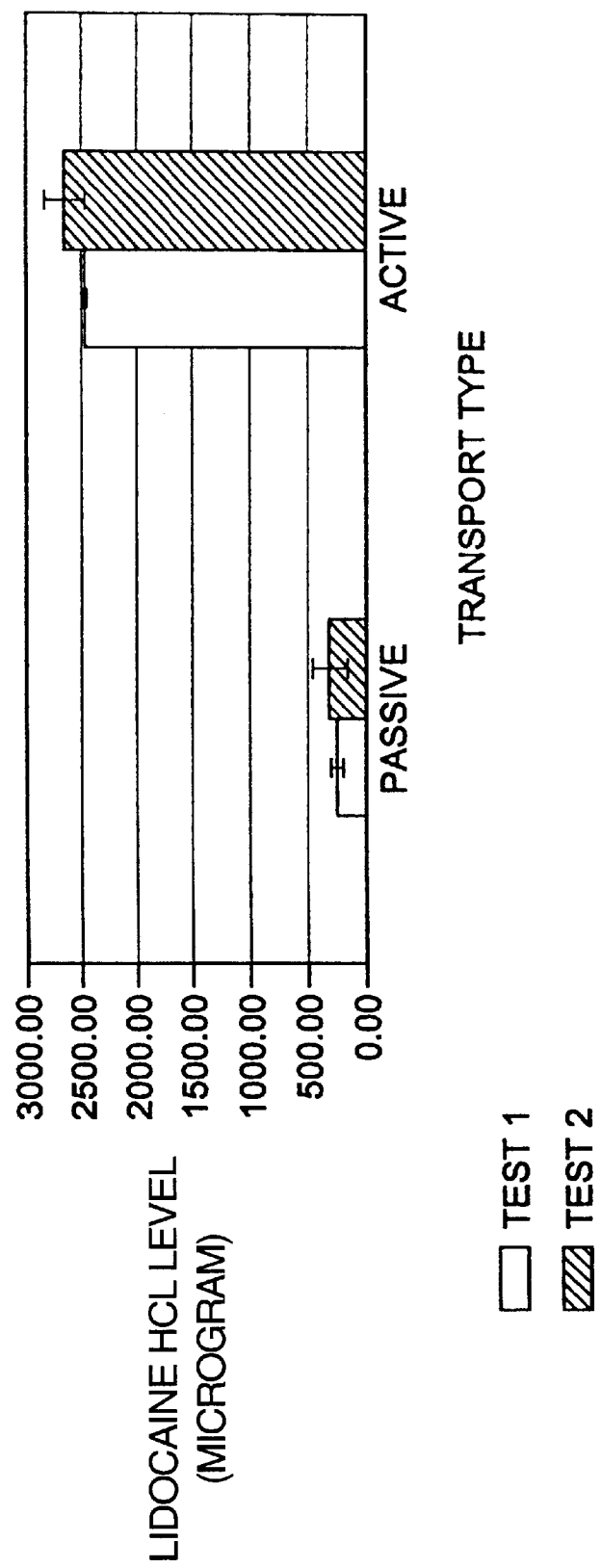
FIG. 8 is a graphical representation of the relative amounts of active versus passive delivery and also illustrates the reproducibility of the method of the invention in another embodiment.

Referring now to FIGS. 7 and 8, comparisons between active (iontophoretic) delivery and passive (diffusive) delivery were made using the preferred ion exchange membrane as a separation medium. In the experiment illustrated in FIG. 7, the ion exchange membrane (Pall, R-4010) was pretreated by exposure to 0.18% (aqueous w/v) calcium chloride ($CaCl_2$) for 24 hours prior to use in the method of the invention as described above. In this example, the ratio of active (iontophoretic/preselected current) delivery to passive (diffusive/ no current) delivery of lidocaine was shown to be 11.6.

Another comparison shown in FIG. 8 using the ion exchange membrane (Pall, R-4010) pretreated with 0.9% aqueous saline (NaCl) for 24 hours showed good reproducibility between duplicate runs for determination of lidocaine in the active and passive delivery.

In the case where NaCl is used as the pretreatment, a ratio of active to passive delivery of about 7.7 is seen.

In a further study on another aspect of the method of the invention, a series of reservoir-electrodes were prepared having lidocaine HCl at several levels and a constant loading of epinephrine bitartrate providing a free base equivalent of 1.05 mg per reservoir-electrode. Five reservoir-electrodes prepared at each of the several lidocaine levels were assayed according to the method described above. The results are given below in Table 3.

TABLE 3

| Lidocaine HCl (mg/unit) | Lidocaine HCl recovered (mg) Mean ± SD, n = 5 | Epinephrine recovered (mg) Mean ± SD, n = 5 |
| --- | --- | --- |
| 100 | 2.46 ± 0.02 | 0.02 ± 0.001 |
| 50 | 2.16 ± 0.02 | 0.041 ± 0.001 |
| 25 | 1.80 ± 0.03 | 0.075 ± 0.002 |

The results shown in Table 3 show that the method of the invention is able to discriminate between reservoir-electrodes loaded with lidocaine hydrochloride at 25, 50 and 100 mg respectively. Additionally, the results in Table 3 suggest that, as the lidocaine HCl level is reduced relative to the constant epinephrine bitartrate level, under the same delivery conditions the amount of epinephrine delivered is increased. This is consistent with the transport theory, where there is a constant applied current, that more of the applied current is carried by other ions in the formulation, i.e., epinephrine, as the lidocaine hydrochloride concentration is decreased.

In the case described above, illustrated schematically in FIG. 4, where a complete iontophoretic device including a controlled power supply, a cathode reservoir-electrode and an anode reservoir-electrode, at least one of which contains at least one ionized medicament for delivery, is desired to be tested, a section of a separation medium may be placed between the cathode and the anode so that each of the cathode and the anode are in intimate electrical contact with the section of separation medium. At this point, the power supply is activated to supply a preselected current flow from one reservoir-electrode to the other as in normal operation. At the completion of the preselected current flow, the separation medium can be removed and assayed for the presence and amount of ionized medicament present. Even in the case where the cathode reservoir-electrode and the anode reservoir-electrode do not have the same size or shape of contact surface, the delivery of the ionized medicament into the separation medium, once characterized, is relatively similar from one complete device to another. Thus the method of the invention is useful for quality control and release testing for function of a complete device.

Another useful application of the method of the invention that utilizes a separation medium to collect a sample for analysis is evaluation of the uniformity of delivery of an ionized medicament by a charged reservoir-electrode. For this evaluation, after the separation medium is subjected to the preselected ionic current, the separation medium may be divided into several individual sections for assay of the delivered medicament. A comparison of the assays of the several individual sections allows a determination of the degree of uniformity of the transport of the ionized medicament across the surface of the reservoir-electrode being studied.

The method of the invention is shown to be useful for a variety of evaluations of iontophoretic components and devices. The use of the separation medium in the method of the invention to acquire an active delivery sample for analysis is readily adaptable for routine evaluation of production components and assemblies, qualification of new materials, changes in manufacturing procedures and for complete systems. The method of the invention is readily compatible with most analytical techniques, automated sampling devices and data acquisition systems.

What is claimed is:

1. A method for testing the ability of an iontophoretic reservoir-electrode to deliver a medicament, the method comprising:
   providing an iontophoretic reservoir-electrode having a contact surface, said iontophoretic reservoir-electrode including an electrical connection and a reservoir including an ionized medicament;
   providing another electrode;
   providing a separation medium having the property of allowing a transport of an amount thereinto of said ionized medicament under the influence of an applied electric current flowing therethrough compared to a transport of an amount of said ionized medicament thereinto in the absence of said applied electric current in a ratio greater than one;
   placing said contact surface of said iontophoretic reservoir-electrode including said ionized medicament in electrical contact with said separation medium;
   placing said separation medium in electrical contact with said another electrode;
   applying a sufficient electrical potential between said iontophoretic reservoir-electrode including said ionized medicament and said another electrode so that a preselected current flows through said separation medium for a preselected time thereby transporting at least a portion of said ionized medicament into said separation medium; and
   determining an amount of said ionized medicament in said separation medium.

2. The method of claim 1 wherein said method further comprises removing said separation medium from said iontophoretic reservoir-electrode and said another electrode prior to said determining step.

3. The method of claim 2 wherein said determining step further comprises extracting said ionized medicament from said separation medium into an eluent and assaying said eluent for said ionized medicament.

4. The method of claim 1 wherein in said step of providing an iontophoretic reservoir-electrode, said reservoir includes more than one ionized medicament, and said determining step comprises determining an amount of each of said more than one ionized medicament.

5. The method of claim 4 wherein in said step of providing an iontophoretic reservoir-electrode, said reservoir includes lidocaine as a pharmaceutically acceptable salt and L-epinephrine as a pharmaceutically acceptable salt.

6. The method of claim 5 wherein in said step of providing an iontophoretic reservoir-electrode, said reservoir includes lidocaine hydrochloride and L-epinephrine bitartrate.

7. The method of claim 1 wherein in said step of providing a separation medium, said separation medium is selected from the group consisting of ion exchange membranes, ion exchange resins, ion exchange beads, polyelectrolyte salts, hydrogels and semipermeable membranes.

8. The method of claim 7 wherein said separation medium is an ion exchange membrane.

9. The method of claim 1 wherein said step of applying a sufficient electrical potential comprises applying a sufficient electrical potential to provide a preselected current profile.

10. The method of claim 1 wherein said placing steps further comprise placing said iontophoretic reservoir-electrode including said ionized medicament, said separation medium and said another electrode into a fixture disposed to apply sufficient pressure to said iontophoretic reservoir-electrode and said another electrode to ensure electrical contact between said electrodes and said separation medium thereby facilitating said preselected current flow.

11. The method of claim 1 wherein said reservoir of said iontophoretic reservoir-electrode includes a net positively charged medicament and said step of applying a sufficient electrical potential comprises applying said potential so that said iontophoretic reservoir-electrode including said net positively charged medicament is operated as an anode when said preselected current is flowing.

12. The method of claim 1 wherein said reservoir of said iontophoretic reservoir-electrode includes a net negatively charged medicament and said step of applying a sufficient electrical potential comprises applying said potential so that said iontophoretic reservoir-electrode including said net negatively charged medicament is operated as a cathode when said preselected current is flowing.

13. The method of claim 1 wherein said preselected time is between about thirty seconds and about ten minutes.

14. The method of claim 13 wherein said preselected time is about one minute.

15. The method of claim 1 wherein said separation medium is nonporous.

16. The method of claim 15 wherein said separation medium is formed from radiation-grafted cast polytetrafluoroethylene, said polytetrafluoroethylene having functional groups capable of ion exchange grafted thereon.

17. The method of claim 1 wherein said step of applying a sufficient electrical potential comprises applying a sufficient potential to cause a higher current flow through said separation medium for said preselected time than would be acceptable in iontophoretic delivery of said ionized medicament to a patient thereby reducing the time required for practicing the method of the invention.

18. A method for testing the ability of an iontophoretic reservoir-electrode to deliver a medicament, the method comprising:

providing an iontophoretic reservoir-electrode, said iontophoretic reservoir-electrode including an electrical connection and a reservoir including an ionized medicament;

providing another electrode;

providing an ion exchange membrane having a first side and a second side, said ion exchange membrane further having the property of allowing passage therethrough of ions of one net charge and substantially preventing the passage of ions of another net charge;

placing said first side of said ion exchange. membrane in electrical contact with said iontophoretic reservoir-electrode including said ionized medicament;

placing said second side of said ion exchange membrane in electrical contact with said another electrode;

applying a sufficient electrical potential between said iontophoretic reservoir-electrode including said ionized medicament and said another electrode so that a current flows through said ion exchange membrane for a preselected time thereby transporting a quantity of said ionized medicament into said ion exchange membrane; and determining an amount of said ionized medicament in said ion exchange membrane.

19. The method of claim 18 wherein said determining step is preceded by removing said ion exchange membrane from said iontophoretic reservoir-electrode.

20. The method of claim 19 wherein said determining step further comprises extracting said ionized medicament from said ion exchange membrane to obtain said ionized medicament in an eluent.

21. The method of claim 20 wherein said determining step further comprises an assay of said eluent to determine an amount of said ionized medicament.

22. The method of claim 19 wherein said determining step is preceded by a dividing step comprising dividing said ion exchange membrane into at least two equal portions and determining an amount of said ionized medicament in each portion, thereby allowing an assessment of a uniformity of the transport of the quantity of said ionized medicament from said iontophoretic reservoir-electrode.

23. A method for testing the ability of an iontophoretic device including a controlled power source, an iontophoretic reservoir-electrode including an ionized medicament and another electrode including a salt, the method comprising:

placing a separation medium between said iontophoretic reservoir-electrode including an ionized medicament and said another electrode so that each of said electrodes is in electrical contact with said separation medium;

operating said power source so that a current flows between said iontophoretic reservoir-electrode including said ionized medicament and said another electrode through said separation medium thereby transporting a quantity of said ionized medicament into said separation medium;

removing said separation medium having-said quantity of said ionized medicament therein; and determining an amount of said ionized medicament in said separation medium.

24. A method for testing the ability of an iontophoretic reservoir-electrode to deliver a medicament, the method comprising:

providing an iontophoretic reservoir-electrode selected to operate at a preselected polarity and having a contact surface, said iontophoretic reservoir-electrode including an electrical connection and a hydrated bibulous reservoir including an ionized medicament;

providing another iontophoretic reservoir-electrode selected to operate at a preselected polarity opposite to said preselected polarity of said iontophoretic reservoir-electrode including said ionized medicament, said another iontophoretic reservoir-electrode having a contact surface and including an electrical connection and a hydrated bibulous reservoir including a salt;

providing an ion exchange membrane having a first side and a second side, said membrane further having the property of allowing passage thereinto of ions of one net charge and substantially preventing the passage of ions of another net charge;

placing said first side of said ion exchange membrane in electrical and physical contact with said contact surface of said iontophoretic reservoir-electrode including said ionized medicament;

placing said second side of said ion exchange member in electrical and physical contact with said contact surface of said another iontophoretic reservoir-electrode;

applying a sufficient electrical potential between said iontophoretic reservoir-electrode including said ionized medicament and said another iontophoretic reservoir-electrode so that a current flows through said ion exchange membrane for a preselected time thereby transporting a quantity of said ionized medicament into said ion: exchange membrane;

removing said ion exchange membrane from said iontophoretic reservoir-electrodes; and determining an amount of said ionized medicament in said ion exchange membrane.

* * * * *